United States Patent [19]

Garson, Jr.

[11] Patent Number: 4,712,554

[45] Date of Patent: Dec. 15, 1987

[54] ELECTRONIC SYSTEM TO DISTINGUISH BETWEEN SINUS AND NONSINUS ATRIAL DEPOLARIZATIONS WHICH DO NOT STIMULATE VENTRICULAR DEPOLARIZATIONS IN RESPONSE TO NONSINUS ATRIAL DEPOLARIZATIONS

[75] Inventor: Arthur Garson, Jr., Houston, Tex.

[73] Assignee: Baylor College of Medicine, Houston, Tex.

[21] Appl. No.: 721,247

[22] Filed: Apr. 8, 1985

[51] Int. Cl.$^4$ ............................................. A61N 1/36
[52] U.S. Cl. ............................................. 128/419 PG
[58] Field of Search ............... 128/419 PG, 696, 702, 128/708, 419 P, 784, 786

[56] References Cited

U.S. PATENT DOCUMENTS

| | | | |
|---|---|---|---|
| 3,138,151 | 6/1964 | Chapman et al. | 128/705 |
| 3,385,289 | 5/1968 | Lawson et al. | 128/700 |
| 3,823,708 | 7/1974 | Lawhorn | 128/700 |
| 3,832,994 | 9/1974 | Bicher et al. | 128/705 |
| 4,059,116 | 11/1977 | Adams | 128/419 PG |
| 4,088,140 | 5/1978 | Rockland et al. | 128/419 PG |
| 4,202,340 | 5/1980 | Langer et al. | 128/702 |
| 4,289,134 | 9/1981 | Bernstein | 128/419 PG |
| 4,303,075 | 12/1981 | Heilman et al. | 128/419 PG |
| 4,343,311 | 8/1982 | Markowitz | 128/419 PG |
| 4,365,639 | 12/1982 | Goldreyer | 128/788 |
| 4,387,717 | 6/1983 | Brownlee | 128/419 PG |
| 4,390,021 | 6/1983 | Spurrell et al. | 128/419 PG |
| 4,403,614 | 9/1983 | Engle et al. | 128/705 |
| 4,421,116 | 12/1983 | Markowitz | 128/419 PG |
| 4,432,362 | 2/1984 | Leckrone et al. | 128/419 PG |
| 4,452,248 | 6/1984 | Keller, Jr. | 128/419 PG |
| 4,458,691 | 7/1984 | Netravali | 128/705 |
| 4,543,963 | 10/1985 | Gessman | 128/702 |
| 4,549,548 | 10/1985 | Wittkampf et al. | 128/419 PG |

*Primary Examiner*—William E. Kamm
*Attorney, Agent, or Firm*—Fulbright & Jaworski

[57] ABSTRACT

An electronic system for maintaining atrio-ventricular synchrony that distinguishes between sinus and nonsinus atrial depolarizations and that stimulates ventricular contraction only when the immediately preceding atrial contraction was a pacemaker stimulated or spontaneous sinus depolarization. Incorporated into the electronic system is a method of determining the sequence of atrial activation to distinguish sinus from nonsinus atrial activations. The atrial activation sequence is determined by comparing the time at which electrical activity is detected at one point in the atrium to the time at which electrical activity is detected at a point in the atrium closer to the ventricle.

17 Claims, 9 Drawing Figures

ELECTRONIC SYSTEM TO DISTINGUISH BETWEEN SINUS AND NONSINUS ATRIAL DEPOLARIZATIONS WHICH DO NOT STIMULATE VENTRICULAR DEPOLARIZATIONS IN RESPONSE TO NONSINUS ATRIAL DEPOLARIZATIONS

BACKGROUND OF THE INVENTION

1. Field of the Invention

The present invention relates to an electronic system that enables distinguishing between sinus and nonsinus atrial depolarizations which, when incorporated into cardiac pacemakers, prevents the pacemakers from stimulating ventricular contractions following nonsinus atrial depolarizations.

2. Description of Related Art

Contraction of cardiac muscle, like all muscle tissue, occurs in response to changes in the electrical potential of the membranes of the muscle cells. When the changes in membrane electrical potentials are recorded and plotted against time, a pattern characteristic of sinus cardiac depolarization is produced. First, a P wave corresponding to depolarization of the atria is seen. A fraction of a second later, a QRS complex corresponding to ventricular activation is observed.

In normal sinus cardiac activation, the wave of electrical depolarization begins in the high right atrium in the sinoatrial (SA) node. From there the wave spreads over the atria in a pattern resembling spreading of waves created by throwing a pebble into water. Located near the juncture of the right atrium and right ventricle is the atrioventricular (AV) node. The wave of depolarization that has spread over the atria converges at the AV node and from there is conducted via specialized conduction fibers to the ventricles resulting in ventricular activation. The delay inherent in conduction from the atria to the ventricles allows sufficient time for atrial contraction to fill the ventricles, and thus maximizes the efficiency of each ventricular contraction.

Because the sequence of atrial and ventricular depolarization observed in normal sinus rhythm optimizes blood flow with each ventricular contraction, maintenance of this sequence is required for continued good health. In a number of disease states, however, normal sinus rhythm is disrupted. For example, when premature ventricular contractions occur, the wave of depolarization begins in a ventricle causing the ventricles to contract before they have been filled with blood from the atrial contraction. If premature ventricular contractions occur too frequently, the reduced amount of blood pumped can be life threatening. Another common abnormal cardiac rhythm is seen when normal conduction from the atria to the ventricles is partially or totally blocked. In these patients, the wave of depolarization begins in the SA node as in normal sinus rhythm, but the wave is not conducted to the ventricles and thus fails to result in the blood being pumped through the pulmonary and systemic vascular systems.

Electronic pacemakers have proved a very effective and reliable treatment modality in patients whose normal sinus rhythms have been disrupted by disease. Many pacemakers in current use that are implanted are dual chambered devices that are capable of sensing and pacing in the atrium and the ventricle. These pacemakers are called "universal" since they can perform almost any function. When the patient's atrial rate falls below a predetermined level, the pacemaker paces the atrium. After a delay sufficient to permit conduction from the atrium to the ventricle, if conduction has not occurred, the pacemaker also paces the ventricle. In many cases the atrial rate is sufficient, however, there is a lack of appropriate AV conduction. In these patients, the pacemaker will sense the patient's own atrial P wave and then pace the ventricle after the P wave.

One of the greatest difficulties in modern pacemaking is that current pacemakers cannot distinguish between sinus P waves and nonsinus P waves. Two major types of nonsinus P waves exist. The first is the "retrograde" P wave. This can occur any time the ventricle is paced by a pacemaker or a premature ventricular contraction occurs with conduction of the ventricular impulse retrogradely to the atrium (retrograde conduction can exist even in a patient with complete antegrade AV block). In this instance, the pacemaker senses the retrograde P wave and responds as though it were a normal sinus P wave. Since the pacemaker is programmed to pace the ventricle after every sensed P wave, an "endless loop" type of pacemaker mediated tachycardia can result. Every time the pacemaker paces the ventricle, it conducts retrogradely to the atrium, is sensed by the pacemaker, and then the pacemaker undesirably paces the ventricle.

Many artificial adjustments are made in current pacemakers in an attempt to circumvent "endless loop" pacemaker mediated tachycardia. The majority of these attempts involve creation of a time during the cardiac cycle when the pacemaker does not sense in the atrium. U.S. Pat. No. 4,343,311 provides an example of this approach. The disadvantages occasioned in creating a time when the pacemaker does not sense in the atrium include patient-to-patient variability in the time delay required, the lack of atrial sensing throughout the entire cardiac cycle, and restricting the upper limit that the pacemaker can pace the ventricle.

The second type of nonsinus P wave is observed in supraventricular tachycardia. In the vast majority of cases of supraventricular tachycardia, the pacemaker senses the P waves and will pace the ventricle at the rate of the P wave. The normal human AV node acts as a filter such that, in the adult, atrial impulses faster than 200 per minute usually will not be transmitted through the AV node to the ventricles. This is a natural event that a pacemaker can circumvent. For this reason, pacemakers have an "upper rate limit" where, regardless of atrial rate, the pacemaker will not transmit impulses to the ventricle above this rate. U.S. Pat No. 4,059,116 discloses a pacemaker that employs an upper rate limit. If supraventricular tachycardia could be distinguished from a normal rapid sinus tachycardia, the artificial "upper rate limit" could be eliminated.

In "retrograde" P waves, the sequence of atrial activiation differs from sinus P waves. In sinus P waves, the atria are activated from the SA node and activation spreads from the high atrium to the low atrium. In "retrograde" P waves, the atria are activated in the reverse direction from low atrium to high atrium. In over 90 percent of supraventricular tachycardias, the atria are activated in a different sequence from sinus rhythm. Therefore, sinus and nonsinus P waves can be distinguished by determining the atrial activation sequence.

In currently used pacemakers, sensing of the atrium is either "unipolar" or "bipolar." In unipolar sensing, there is a single electrode at the tip of the pacemaker lead. This lead usually is placed in the right atrial appendage (RAA) and uses the pacemaker generator as the indifferent electrode. In the bipolar configuration two electrodes are placed approximately 20 mm apart at the end of the lead which also is placed in the right atrial appendage. None of the pacemakers in current use possess a design that enables determining the atrial activation sequence to distinguish between sinus and nonsinus P waves.

SUMMARY OF THE INVENTION

The present invention is directed to apparatuses and methods that distinguish between sinus and nonsinus atrial depolarizations by determing the direction of atrial activation. The invention includes cardiac pacemakers designed to distinguish between sinus and nonsinus atrial depolarizations, which pacemakers stimulate ventricular contractions only when the immediately preceding atrial depolarization was a pacemaker stimulated or spontaneous sinus atrial contraction. According to the present invention, the direction of atrial depolarization is determined by detecting atrial electrical activity at two or more points in the atrium, one point closer to the ventricle than the other. The temporal relationship of the times at which atrial electrical activity is detected at the two points then is compared with the temporal relationship characteristic of sinus atrial depolarizations to distinguish sinus from nonsinus atrial depolarizations.

Accordingly, it is an object of the present invention to provide an apparatus for detecting electrical activity at two points in the atrium and comparing the temporal relationship of the activity so detected to distinguish between sinus and nonsinus atrial depolarizations.

Another object of the present invention is to provide methods for distinguishing between sinus and nonsinus atrial depolarizations by detecting electrical activity at two points in an atrium, one closer to the ventricle than the other, and comparing the temporal relationship of the activity so detected.

A further object of the present invention is to provide cardiac pacemakers that dintinguish between sinus and nonsinus atrial depolarizations and that do not stimulate ventricular depolarizations when the immediately preceding atrial depolarization was a nonsinus atrial depolarization.

A still further object of the present invention is to provide a method of using a cardiac pacemaker to synchronize atrial and ventricular depolarizations wherein ventricular depolarizations are stimulated only when the immediately preceding atrial depolarization was a sinus or pacemaker stimulated sinus atrial depolarization.

Other and further objects, features, and advantages will be apparent from the following description of the presently preferred embodiments of the invention, given for the purpose of disclosure when taken in conjunction with the accompanying drawings.

DESCRIPTION OF THE PREFERRED EMBODIMENTS

The pattern of electrical activity associated with sinus atrial depolarizations differs from that associated with nonsinus atrial depolarizations such as occur following retrograde conduction of electrical activity beginning in the ventricles and that which are observed in supraventricular arrhythmias. Recording atrial electrical activity on a strip chart recorder provides a convenient method for visualizing these differences. Both the morphology (the shape of the electrogram) and the timing of the electrogram are useful parameters to distinguish sinus and nonsinus atrial depolarizations.

As described below, the present inventor has devised several apparatuses and procedures for detecting and utilizing differences in the patterns of atrial electrical activity to distinguish sinus from nonsinus atrial depolarizations. In each of the below examples, an electric lead having at least two or two pairs of electrodes attached near one end is employed to detect atrial electrical activity. The end of the lead bearing the electrodes is positioned within the electrical field created by electrical activity in the atrium. The terms distal electrode or distal electrode pair shall mean the electrode or electrode pair positioned on the lead closest to the end of the lead implanted in the atrial electrical field. The terms proximal or proximal electrode pair shall mean an electrode or electrode pair positioned on the lead at a point farther from the end of the lead placed in the atrial electrical field than the distal electrode or distal electrode pair. Unipolar shall mean a mode of detecting voltage differences between two electrodes wherein one of the electrodes is on the lead placed in the electrical field created by atrial electrical activity and the other is an indifferent electrode outside the field. Bipolar shall mean a mode of detecting voltage differences between two electrodes wherein both electrodes are on the lead placed in the electrical field created by atrial electrical activity.

EXAMPLE 1

Figure 1:
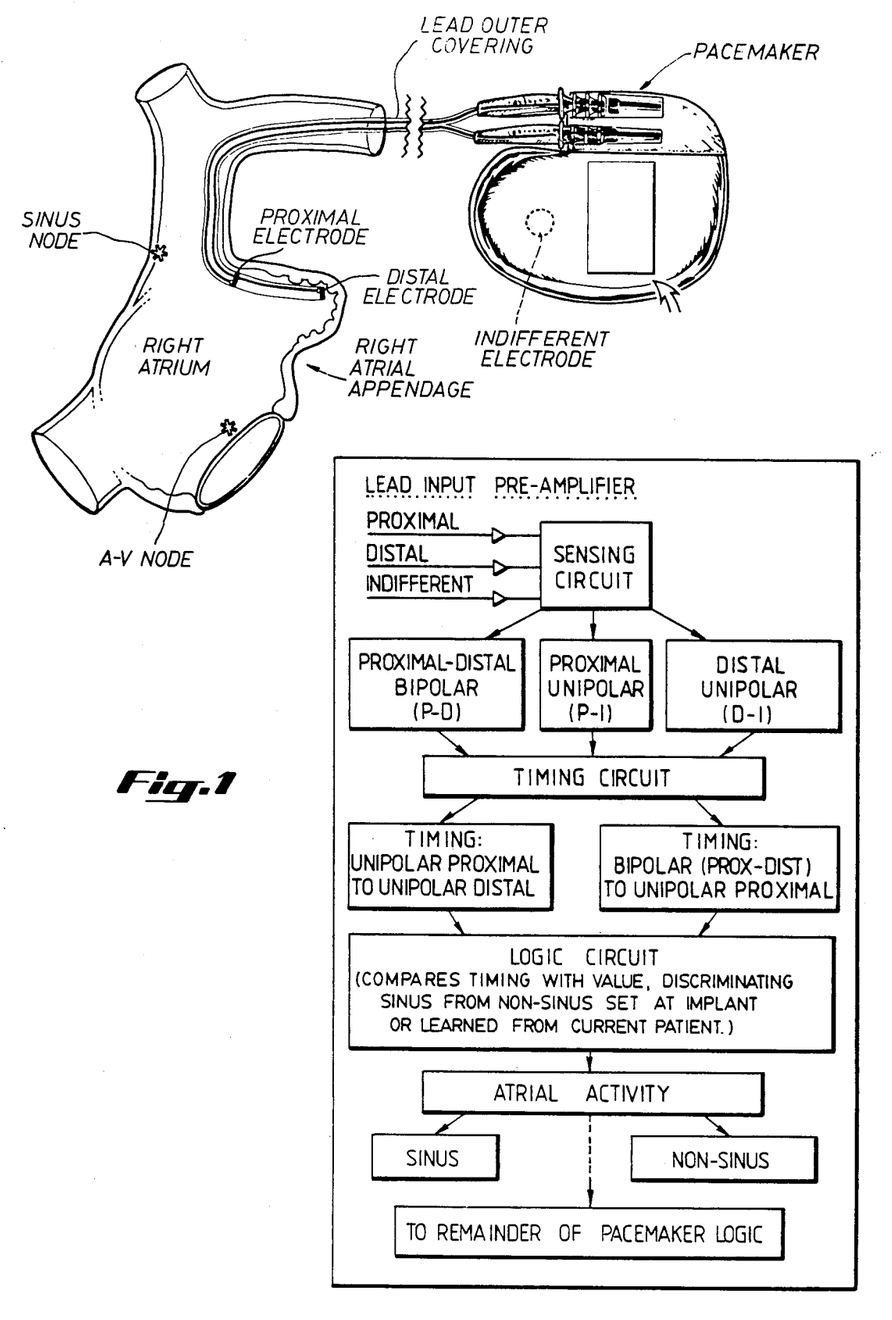
FIG. 1 is a diagram of a pacemaker having a two electrode lead positioned in the right atrial appendage and shows the electronic circuitry of the pacemaker.

Referring now to FIG. 1, a pacemaker 10 with a two electrode sensing/pacing lead 12 is shown with the lead positioned in the right atrial appendage (RAA). Presently, the right atrial appendage is the most common site for placement of pacemaker leads 12. In the "unipolar" configuration, a single electrode close to the site of electrical activation (the electrode on the end of this lead) is compared with a distant "indifferent" electrode. In current pacing, the indifferent electrode is actually the casing of the pacemaker. Therefore, in unipolar sensing, the electrical potential is sensed between two electrodes; one is within the atrial electrical field and the other is distant from this field. In this example, which is the least complicated embodiment of the present invention, unipolar sensing in the right atrial appendage is utilized. A single pacemaker lead 12 having two electrodes 14 and 16 is employed. One electrode 16 is at the distal tip of the lead and the more proximal electrode 14 is several millimeters to centimeters, such as 20 to 40 mm, back from the tip. As is shown in FIG. 1, using this lead 12, there are three inputs to the pacemaker: unipolar from the distal electrode 16, unipolar from the proximal electrode 14, and bipolar between the electrodes.

The diagram of the atrium included in FIG. 1 shows the sinus node 18 (pacemaker of the heart) and the AV node 20 which is the conduction tissue that transmits electrical impulses from the atrium to the ventricle or that transmits impulses retrogradely from the ventricle to the atrium. Activation of the atrium in sinus rhythm begins at the sinus node 18. In contrast, retrograde activation of the atrium begins at the AV node 20. In the unipolar electrode configuration, the proximal 14 and distal 16 electrodes are connected to a lead wire 12 which is connected to the pacemaker. The indifferent electrode is sensed from the pacemaker covering. As shown in FIG. 1, the input goes through a standard pre-amplifier and then to a conventional sensing circuit 22. There are three outputs of the sensing circuit: a bipolar electrogram comparing the potential between the proximal and distal electrodes 24, a unipolar electrogram 26 from the proximal electrode where the potential between the proximal electrode and the indifferent electrode is displayed, and finally the unipolar electrogram 28 from the distal electrode where the potential between the distal electrode and the indifferent electrode is displayed. These electrodes then input into the conventional timing circuit 30, and a time difference in milliseconds is calculated. For these inputs, there are only two times that need be calculated: (1) the timing from the unipolar proximal electrogram to the unipolar distal electrogram, and (2) the timing from the bipolar (proximaldistal electrogram) to the unipolar-proximal electrogram). The bipolar to unipolar distal time is not calculated because it is derived from the other two calculated times.

Once the timing of the atrial electrograms has been calculated above, it is used by a suitable logic circuit 32 to determine whether the atrial activation is sinus or nonsinus. There are two methods available for making this determination. First, if the data are found to be conclusive that, in all patients, there is a consistent numerical difference in these two timings between sinus and nonsinus atrial electrograms, then this numerical difference will be programmed into the pacemaker logic circuit. For example, if in all patients in sinus rhythm the proximal unipolar electrogram is more than 10 milliseconds after the bipolar electrogram and in retrograde activation, the unipolar proximal electrogram is more than 10 milliseconds before the bipolar electrogram, these parameters will be programmed into the pacemaker, and the pacemaker will use these criteria to distinguish between sinus and nonsinus atrial electrograms. On the other hand, it is possible that some patients may have unique differences between their own sinus and nonsinus P waves. In these cases, the pacemaker will be programmed with the times unique to the patients in whom the pacemaker is to be used. In these patients, the pacemaker will use the times unique to the patients to distinguish between sinus 34 and nonsinus 36 atrial electrograms. Returning to FIG. 1, once the pacemaker distinguishes between sinus 34 and nonsinus 36 atrial activity, this information is fed to the remainder of the pacemaker logic 38 which includes conventional ventricular stimulating circuitry and the pacemaker 10 stimulates a ventricular depolarization only when the immediately preceding atrial contraction was a spontaneous or pacemaker stimulated sinus atrial depolarization.

Figure 2:
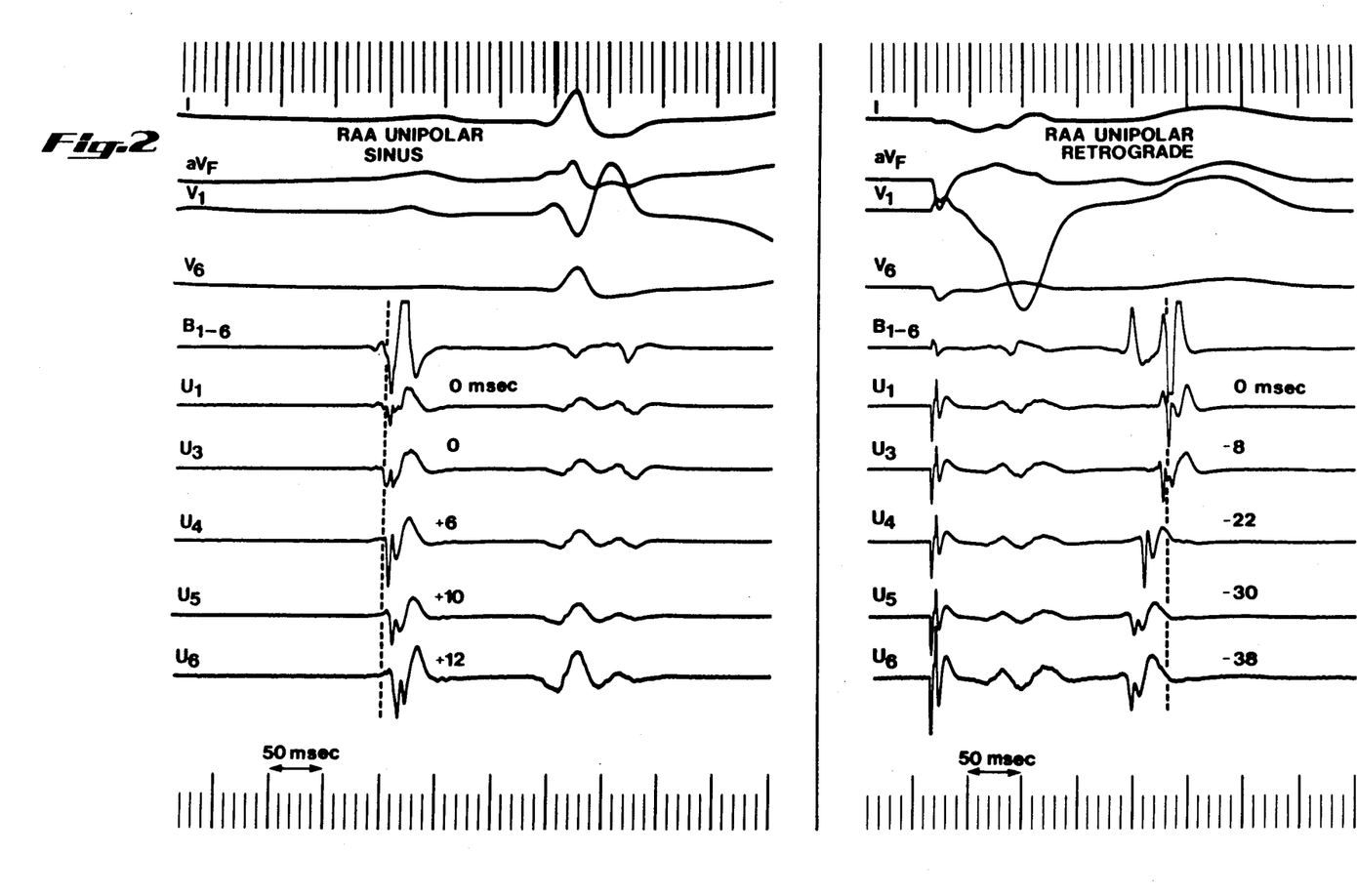
FIG. 2 is a strip chart recording showing the temporal relationship of atrial electrical activity recorded by unipolar sensing and bipolar sensing using the apparatus of FIG. 1.

Testing in more than ten patients has demonstrated that comparing unipolar atrial electrograms to bipolar atrial electrograms provides a reliable method for distinguishing between sinus and nonsinus atrial depolarizations. FIG. 2 demonstrates how strip chart recording of atrial electrograms is used to distinguish between sinus and nonsinus atrial depolarizations. Presently, standard intracardiac electrophysiologic catheters have been used to determine activation sequence. These catheters have between four and ten electrodes embedded in them. Using these catheters, unipolar electrograms can be sensed using any one of the electrodes and bipolar electrograms can be sensed using any two of the electrodes. The electrograms shown in FIG. 2 were recorded from electrodes on the catheter numbered such that the most distal electrode was number 1 and the most proximal electrode was number 6. Each metal electrode is 2 millimeters in width. The distance between members of an electrode pair (1 and 2, 3 and 4, 5 and 6) is 2 millimeters and the distance between pairs is 5 millimeters. Therefore, in this catheter, electrode 1 is at the tip, 2 is 4 millimeters back from the tip, 3 is 11 millimeters back from the tip, 4 is 15 millimeters back from the tip, 5 is 22 millimeters back from the tip, and 6 is 26 millimeters back from the tip.

Using the catheter described above and placed into the right atrial appendage, recordings of sinus and retrograde atrial electrical activity were made and are shown in FIG. 2. The tracing was recorded at 250 millimeters per second. A duration of 50 milliseconds is shown at the bottom of the tracing. Both tracings are organized from top to bottom in the same order. First, there are four surface electrocardiagram leads I, $aV_F$, $V_1$, and $V_6$ and then there are six intracardiac electrograms. The first is the bipolar electrogram taken between the most proximal and the most distal of the electrodes. This is labeled $B_{1-6}$. Then, unipolar electrograms are shown progressing down the page from electrode 1 ($U_1$) through electrode 6 ($U_6$). The unipolar electrogram from electrode 2 has been omitted. In the left panel is the set of electrograms from sinus rhythm (with a rate of 110 per minute), and in the right panel the electrograms recorded during retrograde atrial contraction (at a rate of 120 per minute) are shown. In both tracings, a vertical dotted line 40 is drawn at the point of probable sensing in the bipolar electrogram. The numbers on the tracing are the time, in milliseconds (msec.) of the unipolar electrogram compared to the bipolar electrogram. Positive numbers indicate that the unipolar electrogram occurred later than the bipolar and negative numbers indicate that the unipolar electrogram occurred before the bipolar electrogram. On the left, in sinus rhythm, all of the unipolar electrograms occur simultaneously or after the bipolar tracing, whereas on the right, with a retrograde atrial activation sequence, all of the unipolar tracings occur at the same time or before the bipolar tracing. The greatest degree of separation between the tracings occurs in the most proximal unipolar electrogram which is 12 milliseconds after the bipolar tracing in sinus rhythm and 38 milliseconds before the bipolar electrogram in retrograde atrial activation. Therefore, the difference between these is 50 milliseconds. Note also that the morphology of the bipolar atrial electrogram is entirely different in sinus rhythm compared with retrograde atrial activation This difference also may be used to differentiate the direction of atrial activation.

FIG. 2 shows tracings made with a catheter that had six intracardiac electrodes. The lead attached to a pacemaker capable of distinguishing sinus from nonsinus atrial depolarizations requires only two electrodes. From these two electrodes, three inputs to the pacemaker are made: (1) the bipolar electrogram, (2) a unipolar electrogram from the distal electrode, and (3) a unipolar electrogram from the proximal electrode.

EXAMPLE 2

Figure 3:
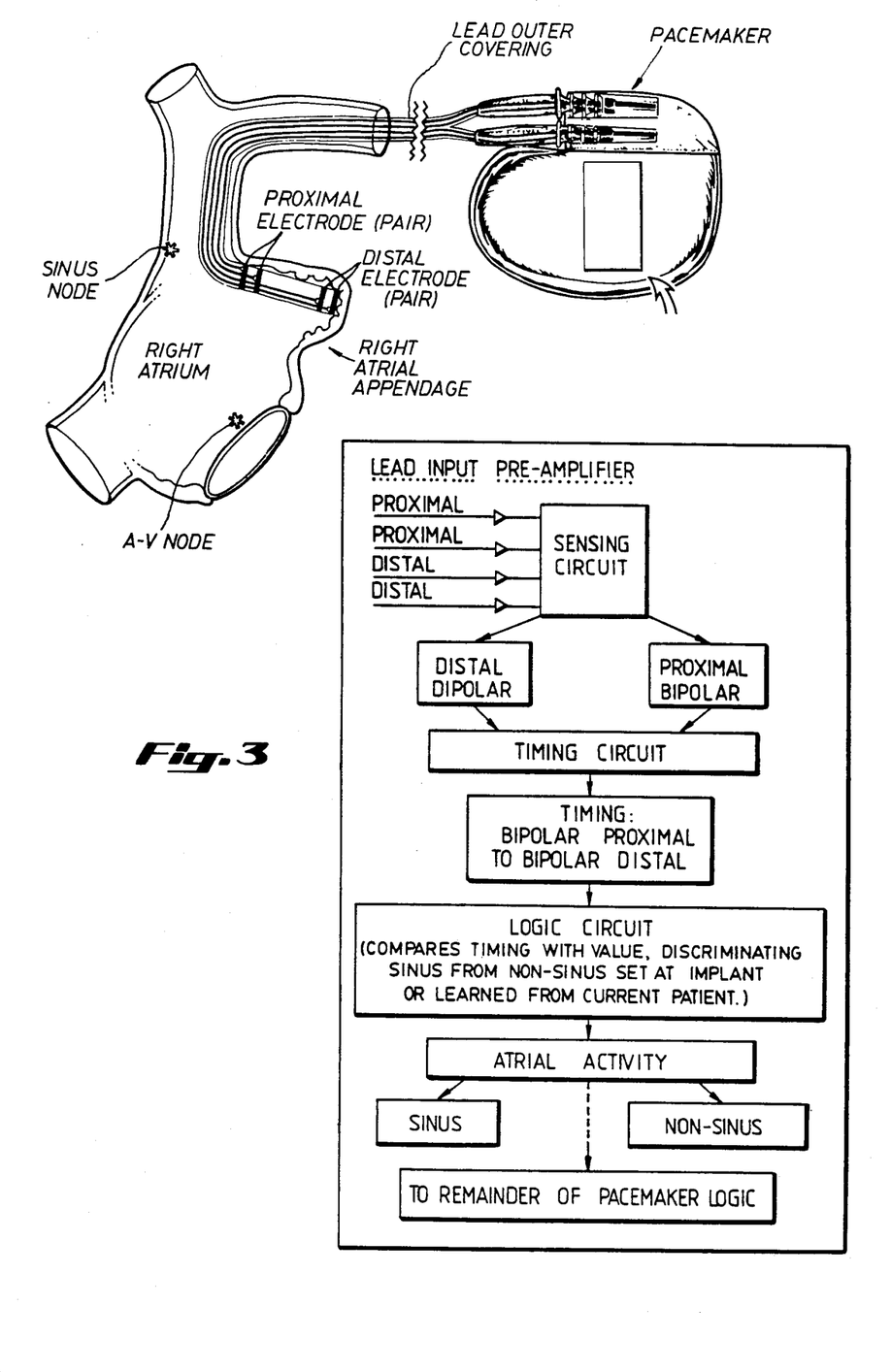
FIG. 3 is a diagram of a pacemaker having a lead with two pairs of electrodes positioned in the right atrial appendage and shows the electronic circuitry of the pace-maker.

Referring now to FIG. 3, a pacemaker having a lead 50 with two pairs 52, 54 of electrodes is shown with the lead placed in the right atrial appendage. This figure also shows a diagram of the pacemaker circuitry used in conjunction with this lead to distinguish between sinus and nonsinus atrial activation. In this example, there are two electrode pairs 52, 54 embedded in the pacemaker lead. The functioning of the circuitry would be similar to that in Example 1 except that the outputs from the sensing circuit 56 would be the electrogram 58 detected at the distal pair of electrodes 54 and the electrogram 60 detected at the proximal pair of electrodes 52 and only the time interval between the electrogram 60 from the proximal electrode pair 52 and the electrogram 58 from the distal electrode pair 54 would be calculated by the timing circuit 62. To indicate that the remaining circuitry would be similar to FIG. 1, numbers corresponding to those of FIG. 1 with an "a" included have been affixed to FIG. 3.

Figure 4:
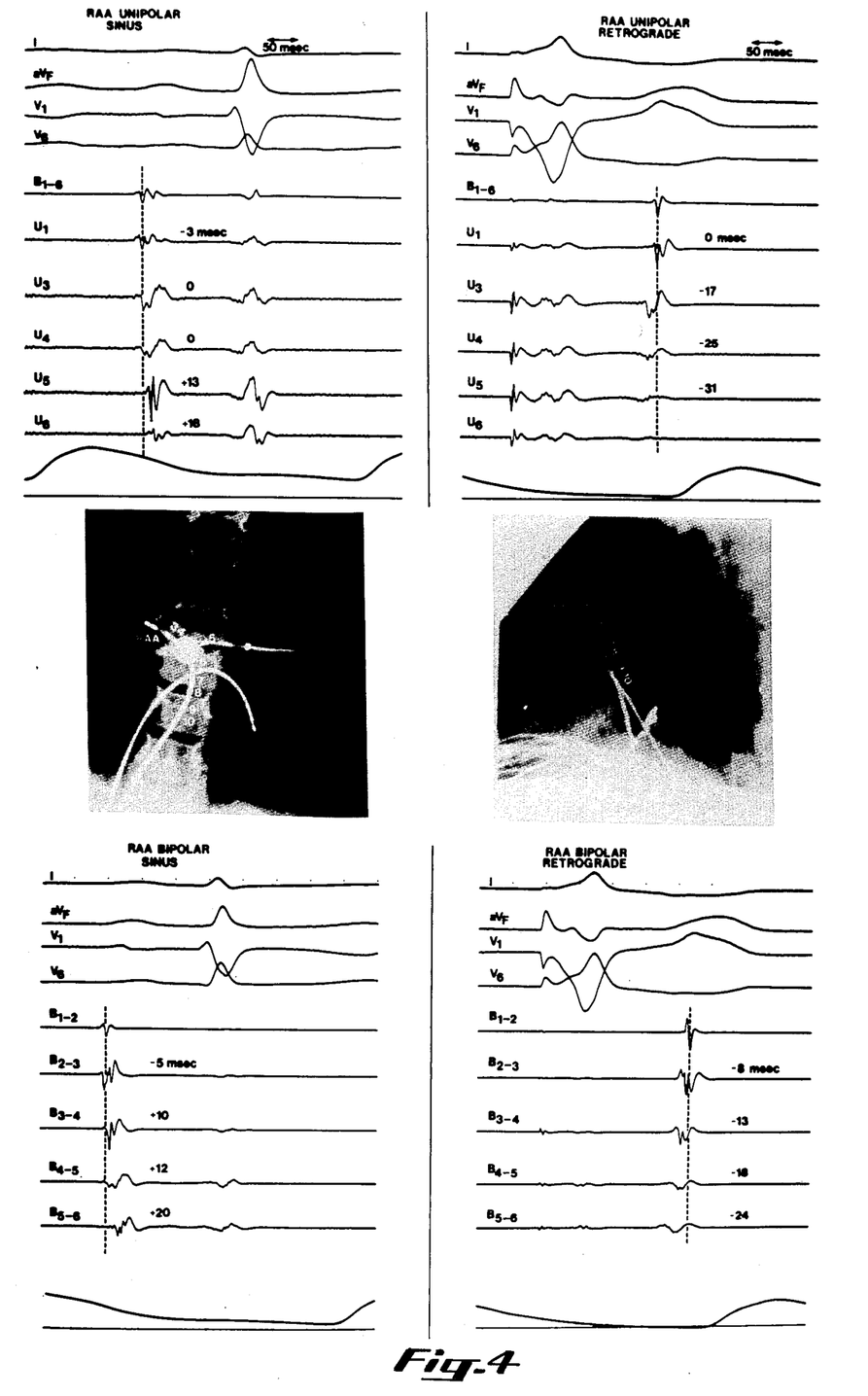
FIG. 4 is a strip chart recording showing the temporal relationships of atrial electrical activity detected by unipolar and bipolar sensing of sinus and retrograde atrial electrical activities using a lead with two electrodes positioned in the right atrial appendage and bipolar sensing using a lead with two pairs of electrodes positioned in the right atrial appendage.

In FIG. 4, electrogram tracings from the right atrial appendage demonstrate the difference between unipolar and bipolar sensing in the right atrial appendage. The catheter used in this example had five pairs of electrodes numbered so that electrode number 1 was at the tip of the catheter and electrode number 10 was most proximal to the tip. Since, in the right atrial appendage, only the first six electrodes are in contact with atrial muscle, only the tracings from these five of the first six electrodes are shown in FIG. 4 ($U_1$, $U_3$–$U_6$). Referring to the top tracings of FIG. 4, in the unipolar electrograms, as in the previous example, the sinus rhythm tracings are later than the bipolar reference and the retrograde tracings are earlier than the bipolar reference. The bottom tracings in FIG. 4 were taken from bipolar pairs of electrodes positioned as shown in FIG. 3. In sinus atrial activity, electrical activity was detected at the proximal bipolar pair of electrodes 52 after the distal bipolar pair of electrodes 54. In contrast, in retrograde atrial activity, activity was detected at the proximal electrode pair 52 before activity was detected at the distal electrode pair 54.

EXAMPLE 3

Figure 5:
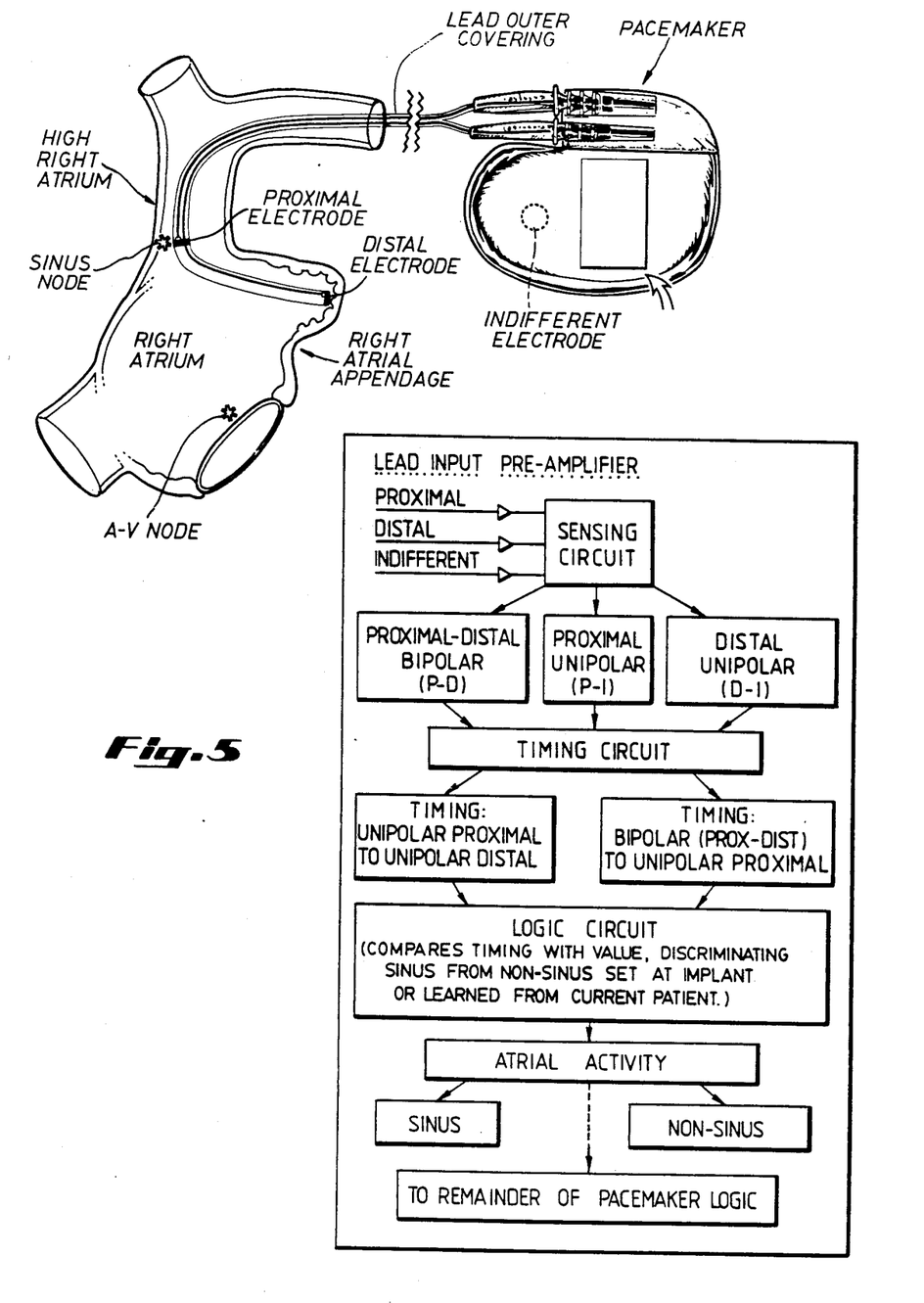
FIG. 5 is a diagram of a pacemaker having a two electrode lead positioned with one electrode in the right atrial appendage and one electrode in the high right atrium and shows the electronic circuitry of the pacemaker.

FIG. 5 shows an embodiment of the present invention wherein the pacemaker distinguishes sinus atrial acitivity from nonsinus atrial activity using an electric lead 70 that has a distal electrode 72 on the tip of the lead 70 placed in the right atrial appendage and a proximal electrode positioned on the lead so that the proximal electrode is in the high right atrium when the distal end of the lead 70 is positioned in the right atrial appendage. Therefore, using this lead, sensing is between the right atrial appendage and the high right atrium. The pacemaker circuitry employed in this example is similar to that in FIG. 1, and has corresponding numerical designations including "b".

Figure 6:
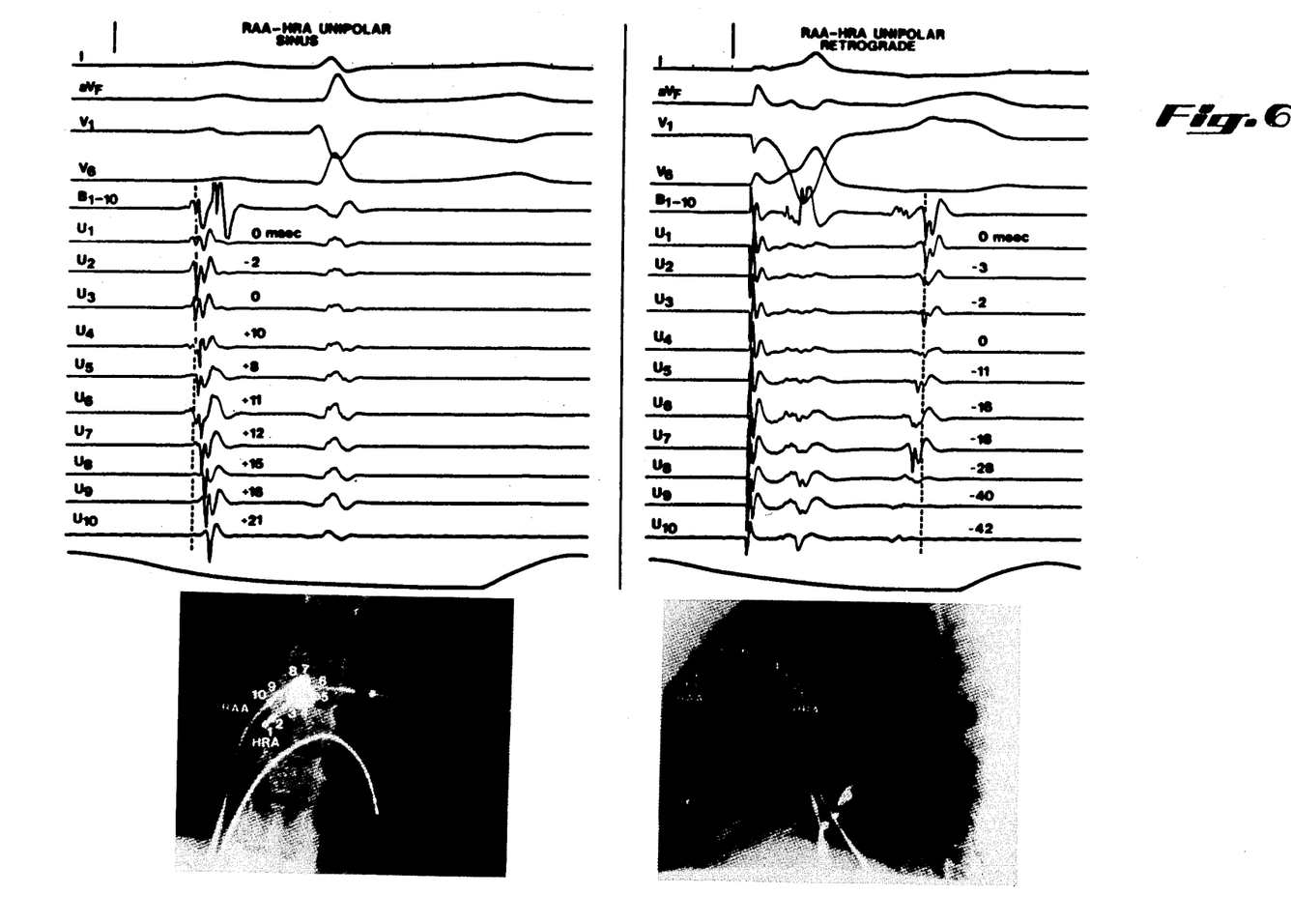
FIG. 6 is a strip chart recording showing the temporal relationship of atrial electrical activity detected by unipolar and bipolar sensing of sinus and retrograde atrial electrical activity using the apparatus of FIG. 5.

FIG. 6 shows electrograms produced by recording from one electrode 72 in the right atrial appendage and another 74 in the high right atrium. Again, for experimental purposes, a multielectrode catheter was used to produce the tracings shown in FIG. 6. As is shown, in sinus rhythm, the unipolar electrogram from the electrode in the high right atrium ($U_{10}$) occurs 21 milliseconds after the onset of the bipolar electrogram ($B_{1-10}$), and in retrograde activation, the unipolar electrogram from the electrode in the high right atrium ($U_{10}$) occurs 42 milliseconds before the bipolar electrogram ($B_{1-10}$). The pacemaker circuitry shown in FIG. 5 uses these time differences to distinguish sinus from nonsinus atrial activity.

EXAMPLE 4

Figure 7:
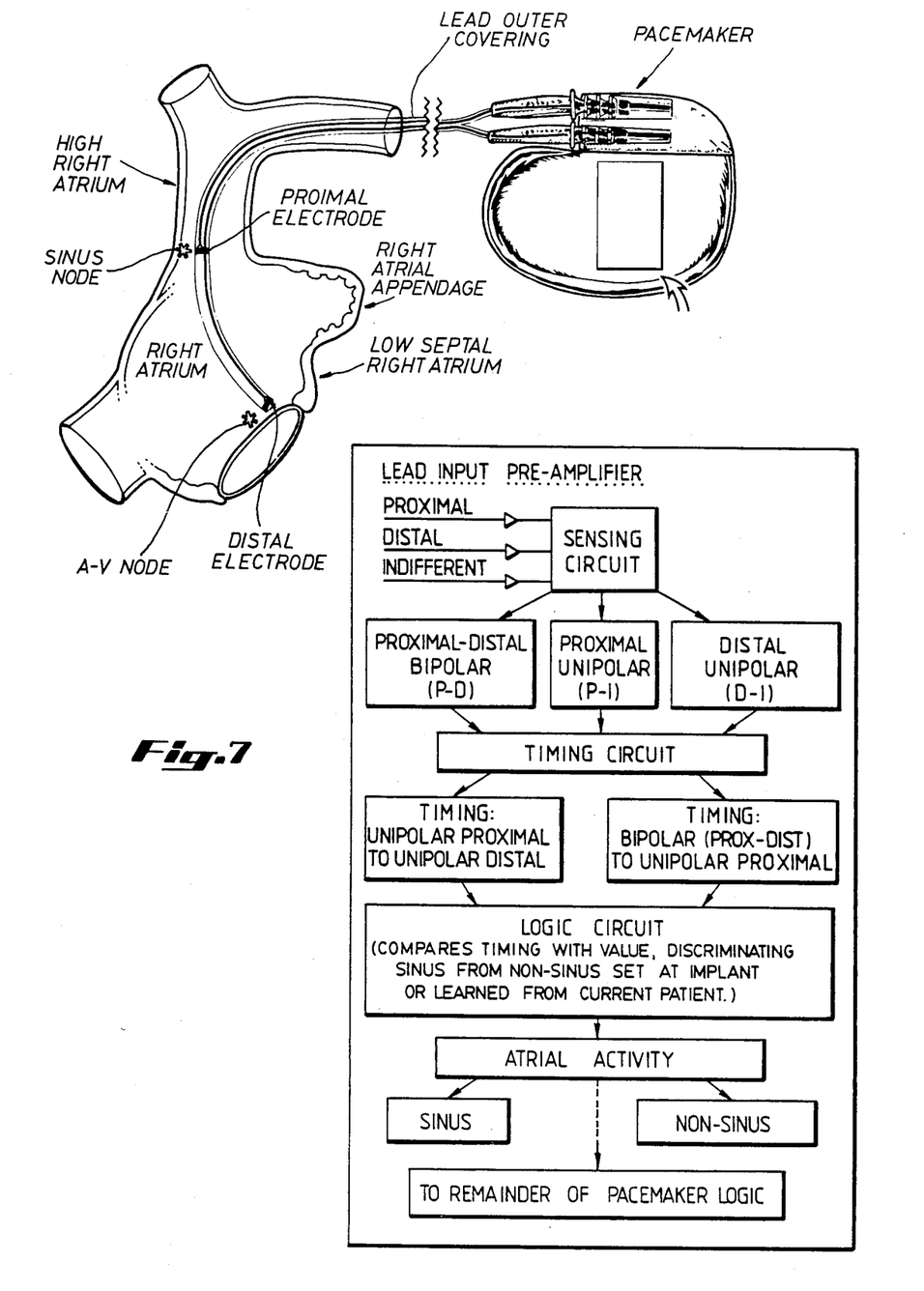
FIG. 7 is a diagram of a pacemaker having a two electrode lead positioned so that one electrode is in the low septal right atrium and the other is in the high right atrium and shows the electronic circuitry of the pacemaker.

FIG. 7 depicts an embodiment of the present invention using an electric lead 80 with the tip positioned in the low septal right atrium rather than in the right atrial appendage as in the previous example. The tip 82 of the lead 80 is secured in the low septal right atrium by affixing the screw tip attached to the lead to the atrial wall. This lead has a distal electrode 84 positioned at the tip of the lead and a proximal electrode 86 positioned on the lead so that, when the tip of the lead is in the low septal right atrium, the proximal electrode is in the high right atrium. Thus, the distal electrode records potentials near the AV node and the proximal electrode records from the high right atrium. FIG. 7 also shows the electronic circuitry of a pacemaker used with this lead that distinguishes between sinus and nonsinus atrial activity. This circuitry is similar to that shown in FIG. 1.

Figure 9:
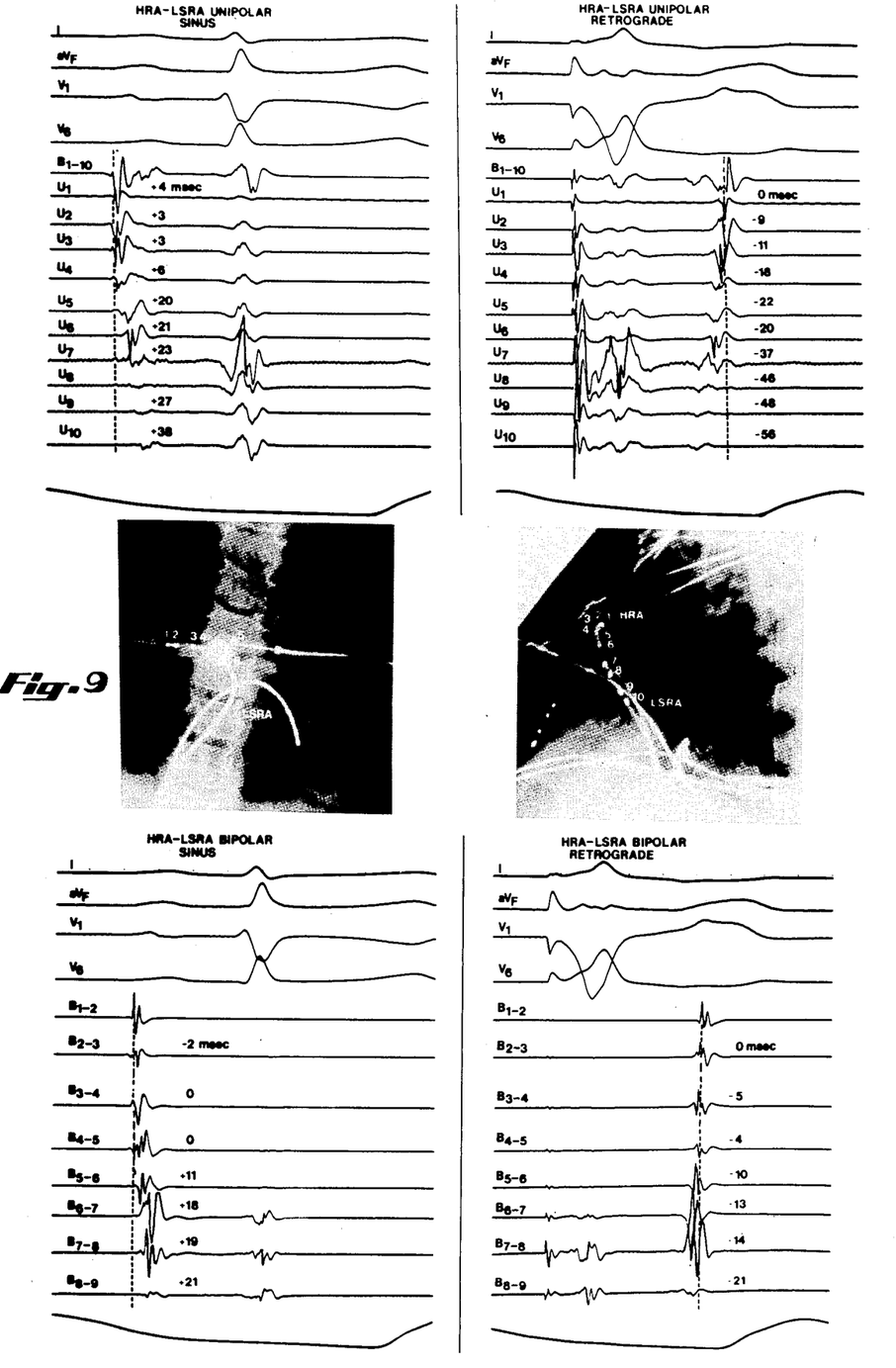
FIG. 9 is a strip chart recording showing the temporal relationship of atrial electrical activity detected by unipolar and bipolar sensing of sinus and retrograde atrial electrical activity using a two electrode lead positioned so that one electrode is in the low septal right atrium and the other is in the high right atrium and by bipolar sensing using a two paired electrode lead positioned so that one pair of electrodes is in the low septal right atrium and the other pair of electrodes is in the high right atrium.

The top two panels of FIG. 9 show the electrograms produced by recording from electrodes positioned as described in this example. As is shown, the proximal unipolar electrogram ($U_{10}$) occurs 38 milliseconds after the bipolar electrogram ($B_{1-10}$) in sinus atrial activity and, in retrograde atrial activity, the proximal unipolar electrogram ($U_{10}$) is detected 56 milliseconds before the bipolar electrogram ($B_{1-10}$). These time differences are used by the pacemaker to distinguish sinus from nonsinus atrial activity

EXAMPLE 5.

Figure 8:
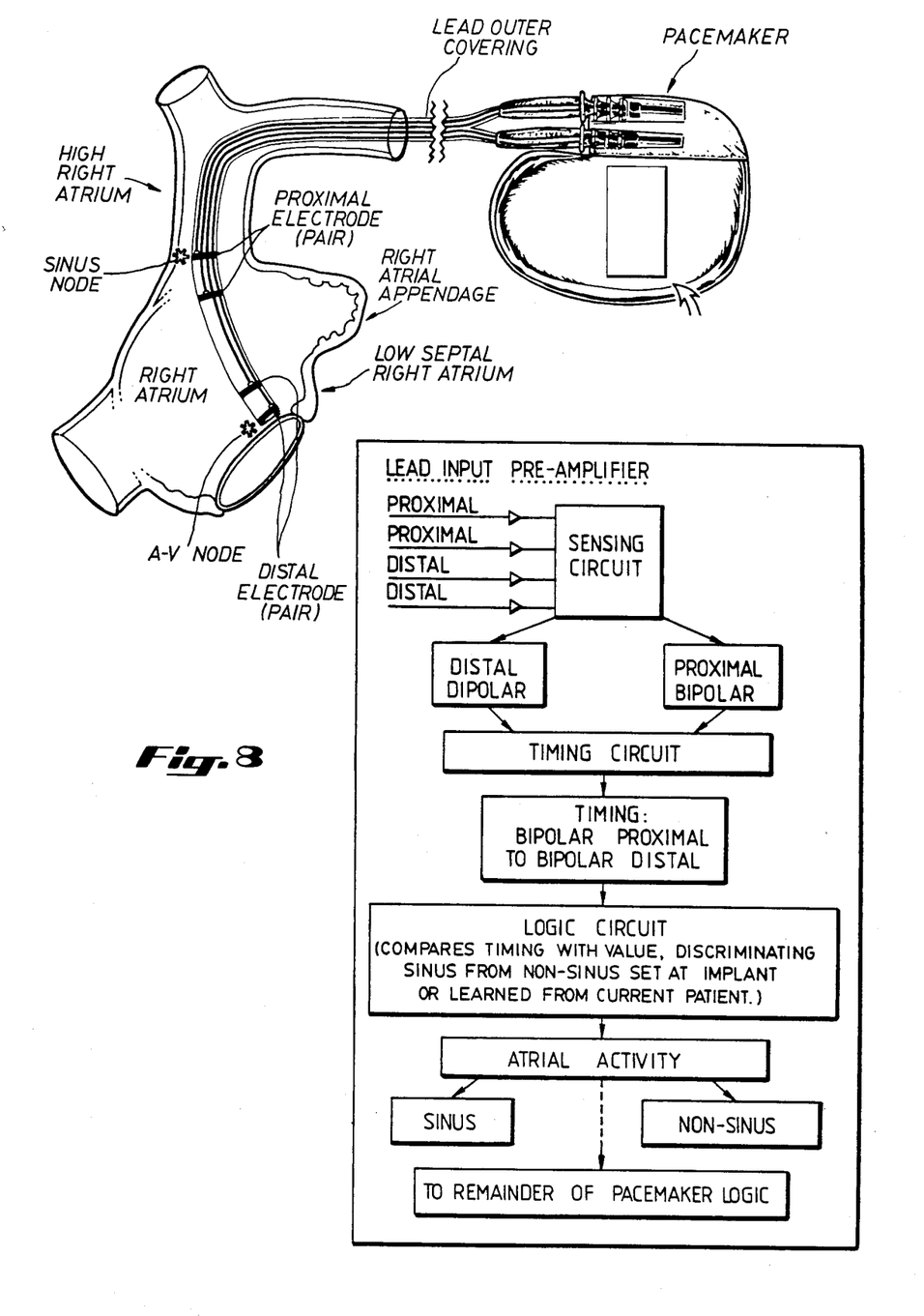
FIG. 8 is a diagram of a pacemaker having a lead with two pairs of electrodes positioned so that one pair of electrodes is in the low septal right atrium and the other is in the high right atrium.

FIG. 8 shows another embodiment of the present invention using a pacemaker with the tip of its lead 90 positioned in the low septal right atrium. In this example, the lead has two pairs of electrodes; one pair 92 is positioned near the tip of the lead in the low septal right atrium, and the other pair 94 is positioned on the lead so that it detects electrical activity in the high right atrium. FIG. 8 also shows the pacemaker circuitry used by a pacemaker equipted with a lead as shown in this example to distinguish sinus from nonsinus atrial activity. This circuitry is similar to that shown in FIG. 3.

The lower panels of FIG. 9 show atrial electrograms recorded using an electric lead positioned in the low septal right atrium so that the distal electrode pair is in the low septal right atrium and the proximal electrode pair is in the high right atrium. As is shown, in sinus atrial activation, electrical activity at the electrode pair in the high right atrium ($B_{8-9}$) is detected 21 milliseconds after electrical activity is detected by the distal electrode pair ($B_{1-2}$). In contrast, in retrograde atrial activation, electrical activity at the electrode pair in the high right atrium ($B_{8-9}$) occurs 21 milliseconds before electrical activity in the distal electrode pair ($B_{1-2}$).

In summary, by using the apparatuses and methods of this invention, sinus atrial activation is distinguishable from nonsinus atrial activation. The ability to make this distinction is useful in diagnosing cardiac rhythm abnormalities Because pacemakers constructed according to the teachings of this invention are able to distinguish between sinus and nonsinus atrial depolarizations, ventricular stimulation following nonsinus atrial contractions is prevented without relying on the many artificial adjustments which must be made in pacemakers in widespread current use.

The present invention, therefore, is well suited and adapted to obtain the objects and ends and has the advantages mentioned as well as others inherent therein.

What is claimed is:

1. An electronic system for pacing a heart that distinguishes between sinus and nonsinus atrial depolarizations and that does not stimulate ventricular depolarizations in response to nonsinus atrial depolarizations, comprising:
    an electric lead having first and second ends;
    at least two electrodes;
    means attaching one electrode to a first end of the lead and means attaching the other electrode to the lead for location in the right atrium when the first end is implanted in the right atrial appendage;
    a sensing circuit including an indifferent electrode connected to the second end of the electric lead, said sensing circuit for detecting voltage difference between one of the electrodes and the indifferent electrode and for detecting voltage difference between the two electrodes;
    a timing circuit connected to the sensing circuit said timing circuit for determining the time interval between the time a voltage difference is detected between one electrode and an indifferent electrode and the time a voltage difference is detected between the two electrodes;
    a logic circuit connected to the timing circuit said logic circuit for comparing the time intervals determined by the timing circuit to time intervals indicative of sinus atrial depolarizations; and
    a ventricular stimulating circuit connected to the logic circuit said ventricular stimulating circuit that does not stimulate ventricular depolarization when the comparison made by the logic circuit indicates that the immediately preceding atrial depolarization was nonsinus said ventricular stimulating circuit effective to stimulate ventricular depolarization only when an immediately preceding atrial contracting is a spontaneous or pacemaker stimulated sinus atrial depolarization.

2. The electronic system of claim 1, where
    the means attaching the other electrode to the electric lead is at a point from 20 mm to 40 mm back from the first end of the lead.

3. The electronic system of claim 2, where
    the means attaching the other electrode to the lead is at a point on the lead sufficiently removed from the first end of the lead so that when the first end of the lead is implanted into the right atrial appendage of a human heart, the other electrode is in the high right atrium.

4. The electronic system of claim 1, where
    the means attaching the other electrode to the lead is at a point sufficiently removed from the first end of the electric lead so that when the first end of the electric lead is implanted into the low septal right atrium of a human heart, the other electrode is in the high right atrium.

5. An electronic system for pacing a heart that distinguishes between sinus and nonsinus atrial depolarization and that does not sitmulate ventricular depolarizations in response to nonsinus atrial depolarizations, comprising:
    an electric lead having first and second ends;
    at least two pairs of electrodes attached to the electric lead near the first end of the lead, the distance between the electrodes of each pair being less than the distance between the pairs of electrodes;
    a sensing circuit connected to the second end of the electric lead said sensing circuit for detecting voltage differences between the electrodes of each of the pairs of electrodes;
    a timing circuit connected to the sensing circuit said timing circuit for determining the time interval between the time a voltage difference is detected between the electrodes of one pair of electrodes and the time a voltage difference is detected between the electrodes of the other pair of electrodes;
    a logic circuit connected to the timing circuit said logic circuit for comparing the time interval determined by the timing circuit to the time interval indicative of sinus atrial depolarizations; and
    a ventricular stimulating circuit connected to the logic circuit said ventricular stimulating circuit that does not stimulate ventricular depolarizations when the comparision made by the logic circuit indicates that the immediately preceding atrial depolarizations was nonsinus said ventricular stimulating circuit effective to stimulate ventricular depolarization only when an immediately preceding atrial contraction is a spontaneous or pacemaker stimulated sinus atrial depolarization.

6. The electronic system of claim 5, wherein
one pair of electrodes is positioned on the lead so that one of the electrodes of this pair is attached to the electric lead at the first end of the lead and the other pair of electrodes is attached to the lead at a point from 20 mm to 40 mm back from the first end of the lead.

7. Method of using a cardiac pacemaker to synchronize atrial activations and ventricular depolarizations, comprising:
obtaining an electric lead having first and second ends that has at least two electrodes attached near the first end of the lead;
positioning the first end of the lead to detect electrical activity in the atrium of the subject;
using a sensing circuit connected to the second end of the lead to detect voltage differences between one of the electrodes and an indifferent electrode and between the two electrodes;
using a timing circuit connected to the sensing circuit to determine the temporal relationship of the time when a voltage difference is detected between one of the electrodes and an indifferent electrode and the time when a voltage difference is detected between the two electrodes;
using a logic circuit connected to the timing circuit to compare the temporal relationship determined in the previous step to the temporal relationship indicative of sinus atrial depolarizations; and
using a ventricular stimulating circuit connected to the logic circuit to stimulate ventricular depolarization only when the comparison made by the logic circuit indicates that the immediately preceding atrial contraction was a spontaneous sinus or pacemaker stimulated atrial depolarization.

8. The method of claim 1 wherein, positioning the first end of the lead to detect electrical activity in the atrium of the subject, comprises:
implanting the first end of the lead in the right atrial appendage.

9. The method of claim 8 including implanting one of the electrodes in the right atrial appendage and the other of the electrodes at a point from 20 mm to 40 mm back from the one of the electrodes.

10. The method of claim 8, including implanting one of the electrodes in the right atrial appendage and the other of the electrodes in the high right atrium.

11. The method of claim 1, wherein positioning the first end of the lead to detect electrical activity in the atrium of the subject, comprises:
implanting the first end of the lead in the low septal right atrium.

12. The method of claim 11, including implanting one of the electrodes in the low septal right atrium and the other of the electrodes in the high right atrium.

13. Method of using a cardiac pacemaker to synchronize sinus atrial depolarizations and ventricular depolarizations, comprising:
obtaining an electrical lead having first and second ends that has at least two pairs of electrodes attached near the first end of the lead;
positioning the first end of the lead to detect electrical activity in the atrium of the subject;
using a sensing circuit connected to the second end of the lead to detect voltage differences between the electrodes of one pair of electrodes and between the electrodes of the other pair of electrodes;
using a timing circuit connected to the sensing circuit to determine the temporal relationship of the time when a voltage difference is detected between the electrodes of one pair of electrodes and the time when a voltage difference is detected between the electrodes of the other pair of electrodes;
using a logic circuit connected to the timing circuit to compare the temporal relationship determined in the previous step to the temporal relationship indicative of sinus atrial depolarizations; and
using a ventricular stimulating circuit connected to the logic circuit to stimulate ventricular depolarizations only when the comparison made by the logic circuit indicates that the immediately preceding atrial contraction was a spontaneous sinus or pacemaker stimulated atrial depolarization.

14. The method of claim 13, wherein positioning the first end of the lead to detect electrical activity in the atrium of the subject, comprises:
implanting the first end of the lead in the right atrial appendage 15. The method of claim 14, including implanting into the right atrial appendage one of the electrodes of one pair of electrodes and the other pair of electrodes from 20 mm to 40 mm back from the first end of the lead.

16. The method of claim 13, wherein positioning the first end of the lead to detect electrical activity in the atrium of the subject, comprises:
implanting the first end of the lead in the low septal right atrium.

17. the method of claim 16, including implanting into the low septal right atrium one of the electrodes of one pair of electrodes attached to the electric lead at the first end of the lead and the other pair of electrodes at a point sufficiently removed from the first end of the lead so that the other pair of electrodes is in the high right atrium.

* * * * *

UNITED STATES PATENT OFFICE
CERTIFICATE OF CORRECTION

Patent No. 4,712,554  Dated December 15, 1987

Inventor(s) Arthur Garson, Jr.

It is certified that error appears in the above-identified patent and that said Letters Patent are hereby corrected as shown below:

Column 2, lines 56-57, "activiation" should read --activation--.

Column 3, line 43, "dintinguish" should read --distinguish--.

Column 4, line 4, "pace-maker" should read --pacemaker--.

Column 7, line 32, "activation" should read --activation.--.

Column 8, line 22, "acitivity" should read --activity--.

Column 9, line 18, "equipted" should read --equipped--.

Column 9, lines 36-37, "abnormalities" should read -abnormalities.-

Column 9, line 61, "difference" should read --differences--.

Column 9, line 63, "difference" should read --differences--.

Column 11, Claim 8, "The method of claim 1" should read
--The method of claim 7--.

Column 11, Claim 9, line 45, "back from the one" should read
--back from one--.

Column 11, Claim 11, "The method of claim 1," should read
--The method of claim 8--.

UNITED STATES PATENT AND TRADEMARK OFFICE
CERTIFICATE OF CORRECTION

PATENT NO. : 4,712,554

DATED : December 15, 1987

INVENTOR(S) : Arthur Garson, Jr.

It is certified that error appears in the above-identified patent and that said Letters Patent is hereby corrected as shown below:

Column 12, Claim 17, line 46, "the method" should read
--The method--.

Signed and Sealed this

Twenty-third Day of August, 1988

Attest:

DONALD J. QUIGG

Attesting Officer

Commissioner of Patents and Trademarks